United States Patent [19]

Whitford

[11] 4,203,065
[45] May 13, 1980

[54] STATE OF CHARGE SENSING MEANS

[75] Inventor: Darryl R. Whitford, Bedford Park, Australia

[73] Assignees: The Flinders University of South Australia; The Minister of Transport, both of Australia

[21] Appl. No.: 922,376

[22] Filed: Jul. 6, 1978

[30] Foreign Application Priority Data

Jul. 8, 1977 [AU] Australia ............................. PD0759

[51] Int. Cl.$^2$ ...................... H02J 7/00; H01M 10/48
[52] U.S. Cl. .................................... 320/43; 320/48; 324/432; 340/636; 429/90
[58] Field of Search ................ 320/43, 48, 39, 40; 324/29, 5; 340/636; 429/90-93

[56] References Cited

U.S. PATENT DOCUMENTS

| | | |
|---|---|---|
| 1,415,385 | 5/1922 | Oswald .............................. 320/43 X |
| 1,988,192 | 1/1935 | Drabin .............................. 320/48 X |
| 2,125,219 | 7/1938 | Campbell ........................... 429/91 X |
| 3,287,175 | 11/1966 | Teed .................................. 340/636 X |
| 3,661,652 | 5/1972 | Ultenbroek ........................ 429/90 |
| 3,683,347 | 8/1972 | Melone ............................. 340/636 X |

*Primary Examiner*—Robert J. Hickey
*Attorney, Agent, or Firm*—Norbert P. Holler

[57] ABSTRACT

Electrolyte from a battery cell is circulated by pump, through a container which contains a hydrometer float, and back to the cell. The float has an opaque neck which interrupts light passing from a light source assembly to a light receiving assembly, and the receiving assembly controls slave means, which can be an illuminated sign, as for example a group of visible light emitting diodes, the number of which illuminated indicating the density of the electrolyte. The slave means can alternatively be a volt meter, or a battery charger, the rate of charge of which is controlled by a voltage signal.

11 Claims, 4 Drawing Figures

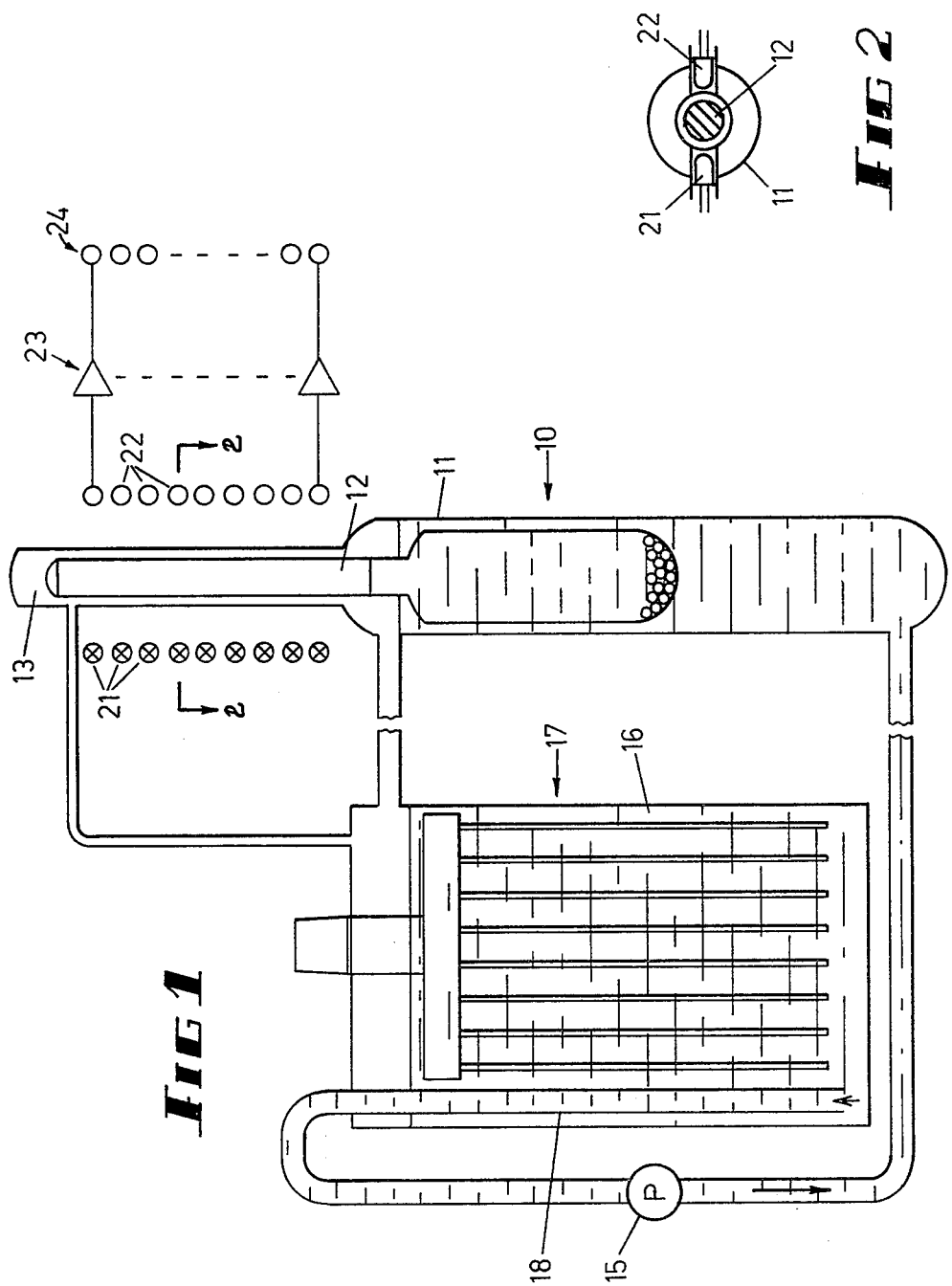

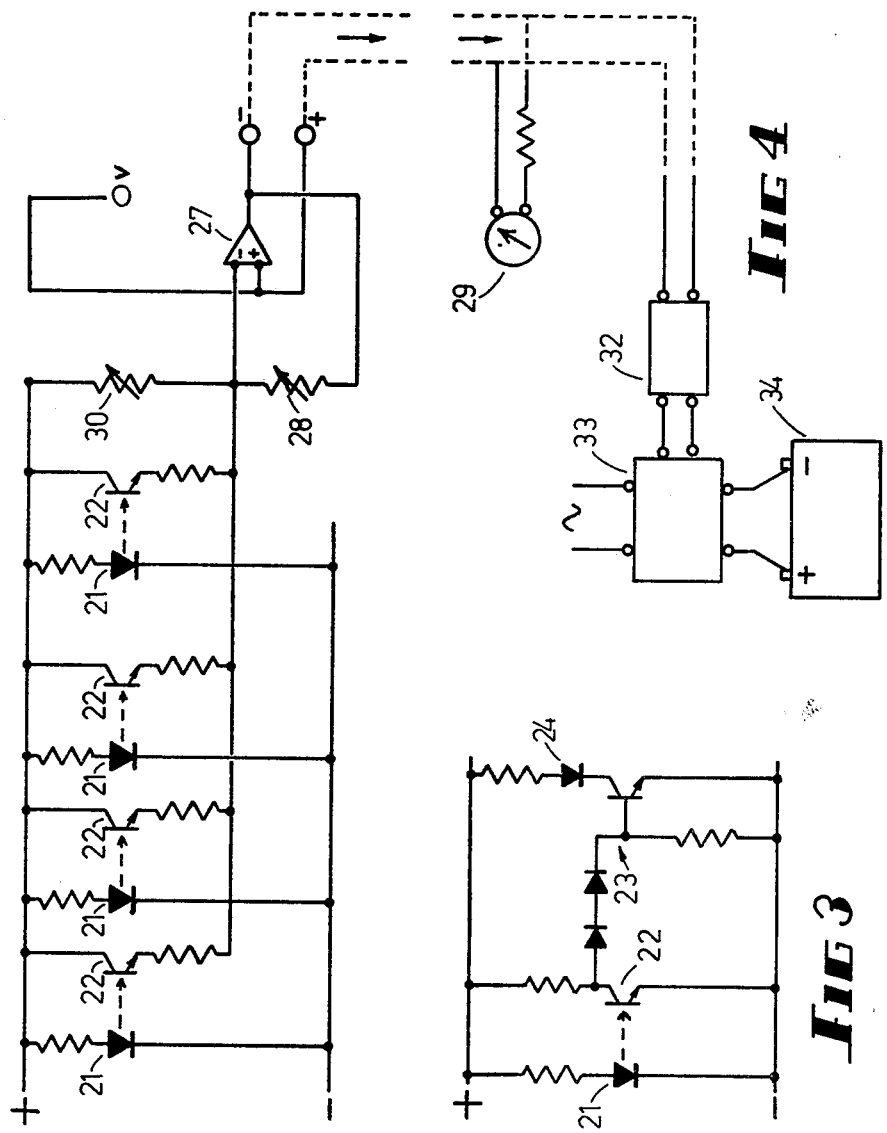

STATE OF CHARGE SENSING MEANS

This invention relates to a sensing means which will sense the state of charge of a rechargable battery cell having a liquid electrolyte the density of which varies as the state of charge and thereby provide a master control for controlling slave means, for example, a readout device, charge indicator means charging rate of battery charger, or other functions.

BACKGROUND OF THE INVENTION

At the present time, there are four main methods used to test the charge of a battery cell:

By far the most common is the method wherein a hydrometer is used to test the electrolyte density, this being the most useful for general purposes since the test is reasonably accurate and can take place under very adverse conditions in the field. However, within a battery cell, stratification of electrolyte takes place, the denser electrolyte remaining near the bottom of the cell and the lighter electrolyte near the top, and because of the construction of most cells, the hydrometer is sensitive only to the upper strata of electrolyte and consequently a battery can, for example, be approaching its fully charged condition, but a hydrometer reading will indicate that it is in a state of greater discharge. This in turn can lead to overcharging of the battery.

Voltage testing in one of two forms can also take place. In one form, the voltage of the cell is sampled, and in this form the test is reasonably accurate but the relationship between voltage and the state of charge is not linear. Another form of voltage check is to check the voltage drop across a sample of electrolyte (this really being a pH check) but this is subject to variation if the electrodes become dirty or contaminated.

Another type of test which has been proposed is one wherein use is made of an electroplate type cell to record the ampere-hours taken out or put into a battery, but there is usually a lag or lead between the actual state of charge and the metal deposit in the cell, and in some instances serious damage has been inflicted upon batteries due to overcharge or over discharge when this method has been used.

A fourth test which has given excellent results in the laboratory has been a test wherein light is passed through a bent tube of glass having a refractive index similar to the refractive index of the electrolyte when in its charged condition, but this test is subject to the disability that the glass surface becomes dirty or contaminated if the test is used under ordinary workshop conditions, and accuracy is lost.

The main object of this invention is to provide a charge sensing means which is sufficiently sensitive to provide an accurate indication of battery charge and sufficiently rugged to provide good results even though conditions are quite adverse.

BRIEF SUMMARY OF THE INVENTION

Briefly, in this invention, electrolyte from a battery cell is circulated by a pump, through a container which contains a hydrometer float, and back to the cell. The float has an opaque neck which interrupts light passing from a light source assembly to a light receiving assembly, and the receiving assembly controls slave means, which can be an illuminated sign, as for example a group of visible light emitting diodes, the number of which illuminated indicating the density of the electrolyte. The slave means can alternatively be a volt meter, or a battery charger, the rate of charge of which is controlled by a voltage signal.

More specifically, one of the aspects of the invention may be defined as consisting of a state of charge sensing means for the sensing of the state of charge of a rechargable battery cell having a liquid electrolyte, comprising:

an electrolyte recirculating circuit comprising an inlet conduit the mouth of which opens into the cell below the electrolyte level, a container, a return conduit extending from the container back to the cell, and a pump operable to recirculate said electrolyte through said circuit, a hydrometer float in said container having an upwardly extending opaque neck the height of which above electrolyte level is a function of electrolyte density, a light source assembly on one side of the opaque neck and a light receiving assembly on the other side of the opaque neck, arranged so that light energy from the light source assembly received by the receiving assembly is a function of said height of the neck, and slave means connected to and controlled by the receiving assembly.

The most convenient light receiving assembly is a transducer assembly comprising a vertical row of photo transistors.

The slave means can, and in most instances will, comprise an amplifier in the output circuit of each phototransistor, which in turn drives a respective light emitting diode, but alternatively it can comprise one or a plurality of fibre optic strands which terminate at their other ends in a readout gauge. If the device is required to be used for controlling charging rate of a cell so that the optimum charging rate is maintained over the whole of the charging cycle, then the output of the or each photo transistor is fed through an operational amplifier which in turn controls the charging voltage and current, either by selecting the voltage tap from a transformer or controlling the phase cut in voltage of the A.C. primary voltage or by other means of controlling the charging rate.

BRIEF DESCRIPTION OF THE DRAWINGS

An embodiment of the invention is described hereunder in some detail with reference to and is illustrated in the accompanying drawings, in which:

FIG. 1 is a diagrammatic elevation of the sensing means,

FIG. 2 is a diagrammatic section taken on line 2—2 of FIG. 1,

FIG. 3 is a circuit diagram illustrating a photo transistor which drives a slave circuit comprising a visible light emitting diode, and FIG. 4 is a circuit diagram wherein the slave circuit makes a summation of output of a plurality of photo transistors to provide a voltage output which is a function of electrolyte density and which controls the charge rate of a battery.

This embodiment is related to a state of charge indicator which is useful particularly on a vehicle powered by a plurality of cells.

A hydrometer float 10 of a type commonly known in the art is housed in a container 11 which allows free upward and downward movement of the hydrometer but guides the hydrometer so that its upwardly projecting neck 12 moves in a vertical direction. Neck 12 is opaque for most of its length, and is movable within a container extension 13, which is transparent.

A small continuous flow pump 15 (of the type suitable for pumping an acid, for example a peristaltic pump or a magnetic centrifugal pump) circulates liquid electrolyte 16 from a cell 17 by drawing the electrolyte from the base of the cell through an inlet conduit 18 and discharging into the container 11, the electrolyte subsequently being discharged from the top of the container 11 back into the top of the cell 17. This feature of the invention avoids the stratification problem referred to previously, since the electrolyte is continuously circulating through the cell. Thus the hydrometer float 10 will continuously indicate not the specific gravity of the least dense electrolyte, but the average specific gravity of the electrolyte in the cell and an accurate "state of charge" will be indicated by the hydrometer float position.

The neck 12 of the hydrometer float 10 is opaque to infra-red light. Aligned along one side of the hydrometer neck is a light source assembly comprising a vertical row of infra-red light emitting diodes 21, aligned with photo transistors of a light receiving assembly which comprises a similar row of infra-red sensitive photo transistors 22 on the opposite side of the transparent container extension 13. The output of the photo transistors 22 is amplified by amplifier circuits 23 (shown in detail in FIG. 3), the output of the amplifiers 23 being used to drive respective visible light emitting diodes 24 in such a sense that if a photo transistor 22 is receiving infra-red light, then the visible light emitting diode will be in an "off" state. If it is not receiving infra-red light, the visible light emitting diode will be in the "on" state. Alternatively, the hydrometer float neck can have an extension thereon with a "window" sumounted by an opaque plate to work in the opposite sense or the amplifier circuits may be arranged to give the opposite sense.

However, in this embodiment, if the hydrometer float 10 is floating high out of the electrolyte under full charge conditions, then all of the photo transistors will be masked from the infrared source due to the opacity of the hydrometer neck 12, and all of the visible light emitting diodes will be "on". As the hydrometer floats lower (less charge) some of the photo transistors will receive infra-red light, so that the visible light emitting diodes at one end will go "off", producing a proportionate remote reading on the gauge having the light emitting diodes. FIG. 3 illustrates only one circuit, but there is a separate circuit for each photo transistor 22 and its visible light emitting diode 24.

In FIG. 3 light emitting diode 21 will cause transistor (OPTO-transistor) 22 to assume an "on" state, the voltage across it being approximately 1-5 v. This voltage is not sufficient to cause foward conduction of the two diodes and therefore transistor 23 remains in the "Off" state. If 22 is mashed from 21, 22 will turn to an "Off" state. The two diodes will forward conduct, drawing current through the resister in the collector circuit of 22, and therefore driving base current through 23, turning to an "on" state. Visible light emitting diode 24 will therefore illuminate. It should be noted that, if the hydrometer float neck 12 is provided with a "window", no amplifier circuit is required between photo transistors 22 and light emitting diodes 24.

The photo transistor outputs may also be used as the input for a simple digital to analog converter, coupled to a volt meter which then will read the level in an analog manner. This arrangement is illustrated in FIG. 4, wherein the infra-red light emitting diodes 21 again energise those photo transistors 22 which are not blanketed by the opaque neck 12, and a summation of the currents $I_1$, $I_2$, $I_3$. . . $I_n$ provides an input to a linear operational amplifier 27, which in this embodiment is a 741 (available from different manufacturers).

Each opto-transistor 22 will cause an input current to the summing input (negative) of the linear operational amplifier. The output voltage of the amplifier will be in proportion to the sum of the input currents. Thus at full charge, when all transistors 22 will be "off" the output voltage of the amplifier will be zero. Resistance 30 may be used to give an adjustment near the zero voltage of "full charge" condition. When all transistors 22 are "on" (minimum state of charge) the maximum output voltage will be obtained from the amplifier. Resistor 28 will adjust the value of this voltage.

The output voltage will be the inverse of the state of charge. A meter may be used directly, graduated in reverse, or the output voltage may be "inverted" by use of another 741 amplifier.

A potentiometer 28 is adjustable to provide minimum needle deflection of voltmeter 29 ("empty" adjustment), and another potentiometer 30 adjusts maximum deflection ("full" adjustment). The voltage output of amplifier 27 passes through a control circuit 22 which controls charging rate of a battery charger 33 for charging the battery 34 at a rate which diminishes as full charge is approached.

The charging and control circuits do not form any part of this invention, and are in accordance with known art. They can, for example, function on the principle of controlling the "cut in" point of the alternating half cycles of the charging current supply, or controlling relays (mechanical or electronic) to control the switching of transformer steps.

If fibre optics are to be used instead of the electronic circuit described above, light emitting diodes replace the infrared emitters.

I claim:
1. State of charge sensing means for the sensing of the state of charge of a rechargable battery cell having a liquid electrolyte the density of which varies in response to the state of charge, comprising:
an electrolyte recirculating circuit comprising an inlet conduit the mouth of which opens into the cell below the electrolyte level, a container, a return conduit extending from the container back to the cell, and a pump operable to recirculate said electrolyte through said circuit,
a hydrometer float in said container having an upwardly extending opaque neck the height of which above electrolyte level is a function of electrolyte density,
a light source assembly on one side of the opaque neck and a light receiving assembly on the other side of the opaque neck, arranged so that light energy from the light source assembly received by the receiving assembly is a function of said height of the neck,
and slave means connected to and controlled by the light receiving assembly.
2. State of charge sensing means according to claim 1 wherein said light source assembly comprises a vertical row of light emitting diodes.
3. State of charge sensing means according to claim 2 wherein said light emitting diodes emit infra-red radiation.
4. State of charge sensing means according to claim 2 wherein said light receiving assembly comprises a verti- cal row of photo transistors which are aligned with respective light emitting diodes.

5. State of charge sensing means according to claim 1 wherein said light receiving assembly comprises a plurality of photo transistors which are progressively exposed to light energy from said light source assembly upon vertical movement of said opaque neck, and wherein said slave means comprises a plurality of amplifiers in the output circuits of respective said photo transistors.

6. State of charge sensing means according to claim 5, and wherein each said amplifier inverts the on/off state of its said photo transistor, and drives a respective visible light emitting transistor.

7. State of charge sensing means according to claim 5, wherein a summation of the outputs of said amplifiers controls a linear operational amplifier, and the output of said linear operational amplifier in turn controls a battery charger to decrease a recharging rate of said cell as the density of its electrolyte increases.

8. State of charge sensing means according to claim 5, wherein a summation of the outputs of said amplifiers controls a readout meter.

9. State of charge sensing means according to claim 1 wherein said slave means comprises a plurality of optical fibres each of which terminates at one end adjacent said opaque neck and form said light receiving assembly, and each of which terminates at its other end at a read-out locality.

10. State of charge sensing means according to claim 1 wherein said light source assembly comprises a vertical row of light emitting diodes, said light receiving assembly comprises a vertical row of photo transistors, and said slave means comprises a plurality of visible light emitting diodes directly coupled by respective conductors to respective said photo transistors.

11. State of charge sensing means according to any preceding claim wherein said opaque neck surmounts a portion of said hydrometer float which does not inhibit passage of light energy from said light source assembly to said light receiving assembly.

* * * * *